Aug. 26, 1952 M. L. WHISLER Plant Pat. 1,123
ROSE PLANT
Filed Jan. 15, 1951
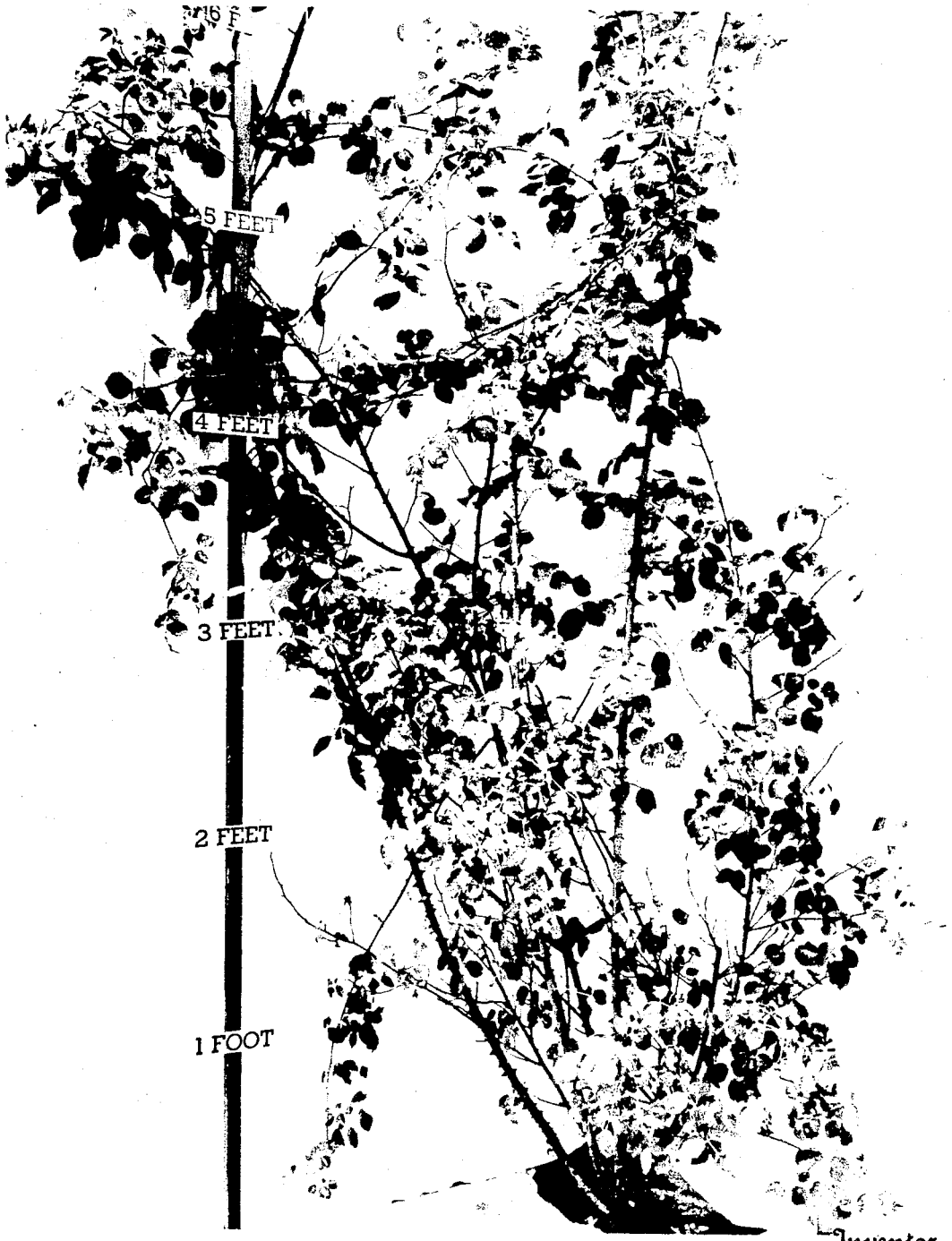
Inventor.
Milton L. Whisler
By Robb & Robb
Attorneys.

Patented Aug. 26, 1952

Plant Pat. 1,123

UNITED STATES PATENT OFFICE 1,123

ROSE PLANT

Milton L. Whisler, Van Nuys, Calif., assignor to Germain's, Inc., Van Nuys, Calif., a corporation of California Application January 15, 1951, Serial No. 205,995

1 Claim. (Cl. 47—61)

The present invention relates to a new and distinct variety of rose plant of the climbing hybrid tea class, originating as a sport of the variety "San Fernando" (Plant Patent No. 785), and dominantly distinguished therefrom by its climbing habit of growth. The new variety was discovered by me in a cultivated field of "San Fernando" plants growing on property controlled by my assignee.

The parent variety is a bush rose of the hybrid tea class, and is notable for its profuse blooming habit, continuity of blooming throughout the season, even in hot weather, the distinctively attractive color of the flowers, and the retention of their form and color until they fall. However, this bush parent has never, so far as I am aware, exhibited a climbing habit, and its growth has been that of the average strong bush rose.

The new variety is substantially identical with its parent except that it is definitely a climber, and in addition, it generally blooms the first year instead of delaying until the second year as do most other climbers. In view of the similarity in general characteristics in respect to the foliage, buds, flowers, wood, etc., of the new variety, as compared with its parent, it is unnecessary to describe the new variety in detail since it conforms to the description contained in the above-noted patent, to which reference may be readily made.

Asexual reproduction by budding at Van Nuys, California, shows that the foregoing characteristics of the new variety come true to form and are established and transmitted through succeeding propagations.

The accompanying drawing shows a specimen plant of the new variety in association with a marked scale, and illustrates the typical climbing habit of growth of the new variety.

I claim:

A new and distinct variety of rose plant of the climbing hybrid tea class, characterized by being substantially identical with its parent "San Fernando" (Plant Patent No. 785), but distinguished therefrom by its climbing habit of growth, and by its habit of blooming the first year, substantially as shown and described herein.

MILTON L. WHISLER.

No references cited.